United States Patent [19]

Kersten

[11] 4,226,124
[45] Oct. 7, 1980

[54] PRESSURE ISOLATOR

[75] Inventor: Jean Kersten, Brussels, Belgium

[73] Assignee: Baxter Travenol Laboratories, Inc., Deerfield, Ill.

[21] Appl. No.: 26,621

[22] Filed: Apr. 2, 1979

[51] Int. Cl.³ .............................................. G01L 7/08
[52] U.S. Cl. ...................................... 73/706; 73/715; 128/214 E; 128/DIG. 13; 210/90
[58] Field of Search ............. 73/706, 715; 128/214 E, 128/DIG. 13; 422/48; 210/90

[56] References Cited

U.S. PATENT DOCUMENTS

| | | | |
|---|---|---|---|
| 2,385,382 | 9/1945 | Samiran | 73/706 |
| 2,948,151 | 8/1960 | Astl | 73/715 |
| 4,077,882 | 3/1978 | Gangemi | 210/90 |

FOREIGN PATENT DOCUMENTS 580140 7/1959 Canada ..................................... 73/715

Primary Examiner—Donald O. Woodiel

Attorney, Agent, or Firm—Paul C. Flattery; George H. Gerstman

[57] ABSTRACT

Apparatus for protecting a pressure sensitive transducer in an extracorporeal blood system and for providing a sterile barrier while the apparatus transmits the blood pressure to the pressure sensitive transducer. The apparatus includes a pressure chamber having a lateral inlet and a lateral outlet, to enable convenient packaging, and having a membrane disposed transverse the chamber and surrounded by the chamber to segregate an inlet side of the chamber from the outlet side of the chamber. The membrane has a generally planar, circular center portion which lies in a plane between the outer peripheral portion of the membrane and the outlet side of the chamber. The membrane has an intermediate portion contiguous with and between the central portion and the outer peripheral portion, with the intermediate portion having a generally U-shaped cross-sectional configuration. The central portion has a substantially greater thickness than the thickness of the intermediate portion, providing a superior displacement of the membrane during operation.

12 Claims, 5 Drawing Figures

PRESSURE ISOLATOR

BACKGROUND OF THE INVENTION

The present invention concerns an improved apparatus for isolating a pressure sensitive device from blood flowing in an extracorporeal blood system and for transmitting the blood pressure to the pressure sensing device.

In a typical extracorporeal blood system, such as dialysis or oxygenation for example, blood is pumped from a patient through a bubble trap, through the mass transfer device (such as the dialyzer or the oxygenator), through a bubble trap and back to the patient. The blood pressures in the line are typically monitored using one or more pressure sensitive transducers. The transducers are isolated from the blood flow line by means of a isolating device which may be coupled between the blood flow line and the pressure sensitive transducer. The isolating device must be operable to protect the transducer, to provide a sterile barrier and to transmit the blood pressure to the transducer.

One type of isolating and blood pressure transmitting device is disclosed in Gangemi, U.S. Pat. No. 4,077,882, issued Mar. 7, 1978. I have discovered an isolating device that is superior in construction and operation with respect to the device disclosed in the Gangemi U.S. Patent, in that the present invention is more compact in construction and thus provides packaging advantages, has a construction which leads to a superior membrane displacement thus resulting in less head pressure losses and a more accurate pressure transmission, and has a construction which provides a significantly greater air volume displacement for a full membrane displacement.

Therefore, it is an object of the present invention to provide an isolating and blood pressure transmitting device that is simple in construction and is easy to manufacture.

Another object of the present invention is to provide an isolating and blood transmitting apparatus that is compact in construction and provides packaging advantages.

A further object of the present invention is to provide an isolating and blood transmitting apparatus that may be produced either by injection molding or thermoforming.

A still further object of the present invention is to provide isolating and blood transmitting apparatus that enables a relatively accurate pressure transmission.

Another object of the present invention is to provide an isolating and blood transmitting apparatus that has a relatively large air volume displaced for the full membrane displacement, enabling the apparatus to be connected to a pressure-monitoring device having a large internal volume, or enabling use with a long connecting tube without sacrificing the precision and the upper limit of the applicable pressure.

Other objects and advantages of the present invention will become apparent as the description proceeds.

BRIEF DESCRIPTION OF THE INVENTION

In accordance with the present invention, an apparatus is provided for isolating a pressure sensitive device from blood flowing in an extracorporeal blood system and for transmitting the blood pressure to the pressure sensing device. The apparatus includes a pressure chamber having an inlet and an outlet for coupling to the pressure sensing device and a membrane disposed transverse the chamber and surrounded by the chamber to segregate an inlet side of the chamber from an outlet side of the chamber. The membrane is fluid impermeable and has its outer peripheral portion connected to the surrounding housing.

The improvement comprising the membrane having a generally planar, circular central portion lying in a plane between the outer peripheral portion and the outlet side. The membrane has an intermediate portion contiguous with and between the central portion and the outer peripheral portion. The intermediate portion extends from the outer peripheral portion in the direction of the inlet side and turns to have a curved portion contiguous with the circumference of the circular central portion. In this manner, the intermediate portion has a generally U-shaped cross-sectional configuration with one side of the U being contiguous with the outer peripheral portion, the other side of the U being contiguous with the central portion and the bight of the U being located in a plane between the outer peripheral portion and the inlet side.

In the illustrative embodiment, the central portion has a substantially greater thickness than the thickness of the intermediate portion. The inlet includes an inlet fitting which extends generally perpendicular to the axis of the pressure chamber and the outlet includes an outlet fitting which extends generally perpendicular to the axis of the pressure chamber. In the illustrative embodiment, the outlet fitting comprises a male luer connector.

A more detailed explanation of the invention is provided in the following description and claims, and is illustrated in the accompanying drawings.

DETAILED DESCRIPTION OF THE ILLUSTRATIVE EMBODIMENT

Figure 1:
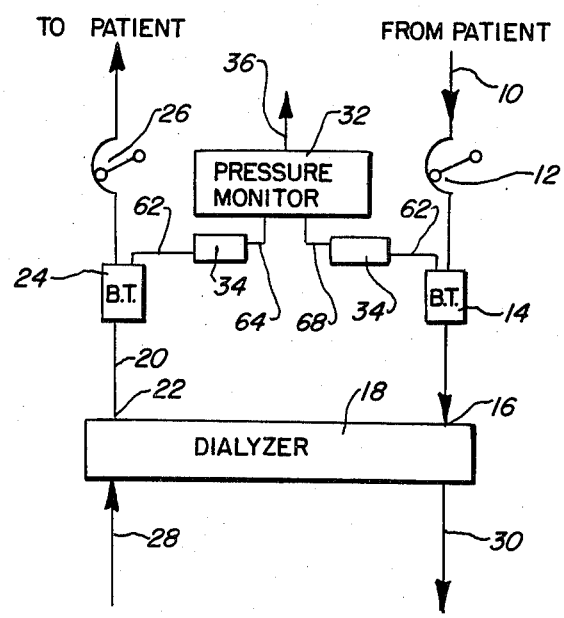
FIG. 1 is a diagram of a type of blood system to which the present invention is applicable.

Referring to FIG. 1, a diagram of an extracorporeal blood system is shown therein. This system includes an inlet blood line 10 from the patient, through a peristalic pump 12 and a bubble trap 14 to the blood inlet 16 of a dialyzer 18. A blood outlet 20 is coupled to the dialyzer blood outlet 22 and conveys the blood through bubble trap 24 and peristalic pump 26 back to the patient. Dialysate fluid is pumped to the dialyzer via line 28 and from the dialyzer via line 30.

The blood pressures are measured by a pressure monitor 32 which includes a pressure sensitive transducer for each blood line under consideration. The pressure sensitive transducers are isolated from the blood lines by means of blood pressure isolators 34, each of which is coupled between a bubble tube inlet and a pressure sensitive transducer. One or more outlets 36 from the pressure monitor is utilized to transmit an appropriate signal to control the blood flow in the appropriate blood line.

Figure 2:
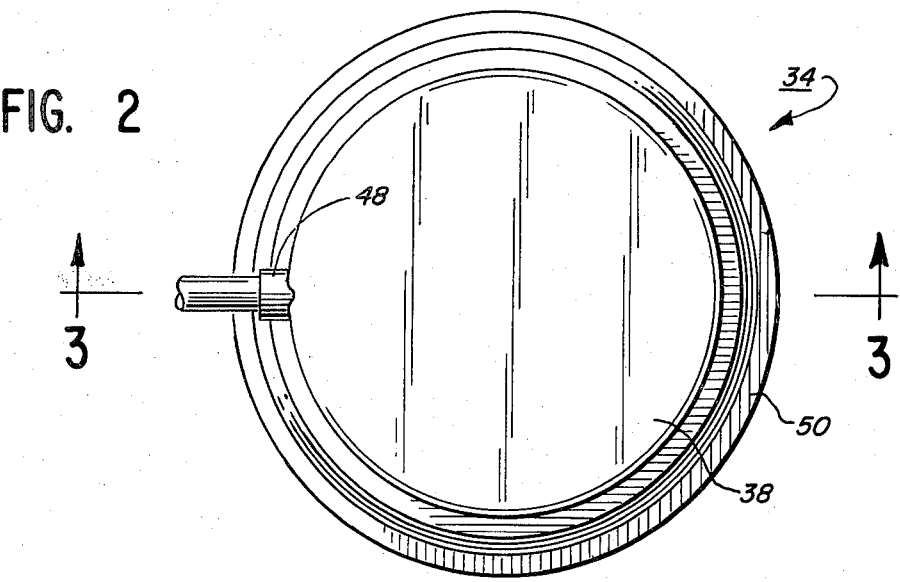
FIG. 2 is a top plan view of isolating apparatus constructed in accordance with the principles of the present invention.
Figure 3:
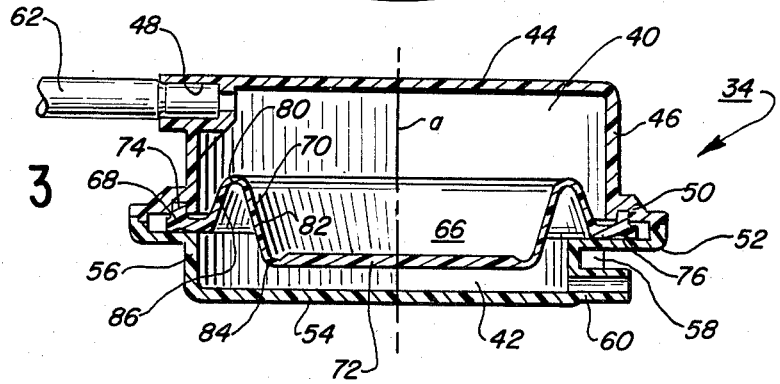
FIG. 3 is a cross-sectional view thereof, taken along the plane of the line 3—3 of FIG. 2.
Figure 4:
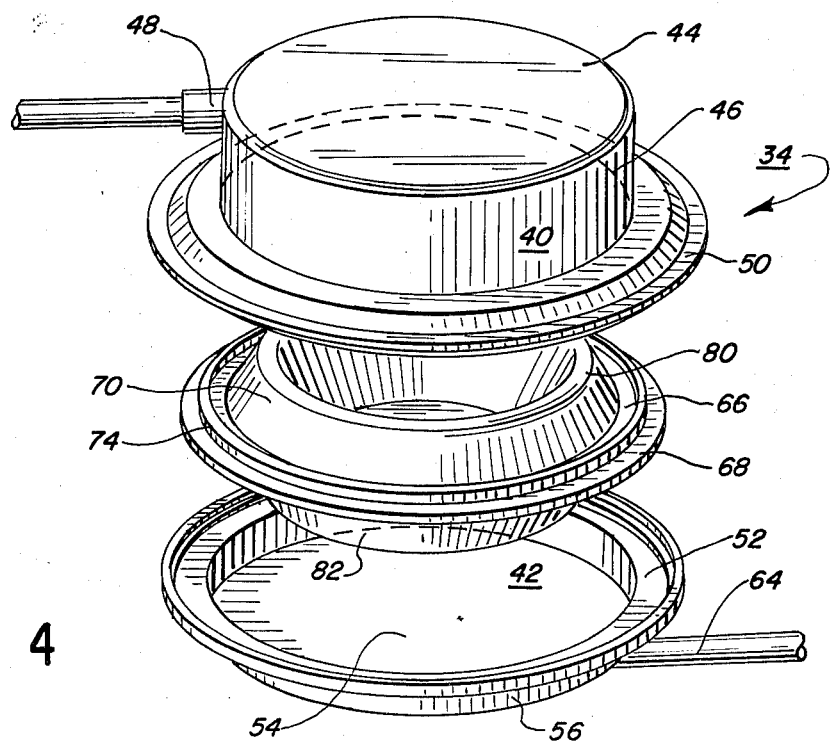
FIG. 4 is an exploded prospective view of an isolating apparatus constructed in accordance with the principles of the present invention.

A blood isolating device 34 constructed in accordance with the principles of the present invention is illustrated in FIGS. 2–4. Referring to these figures, device 34 comprises a plastic pressure chamber 38 including an inlet portion 40 and a mating outlet portion 42. Inlet portion 40 is generally cup-shaped having a top wall 44 and downwardly depending side walls 46 and defining a recessed inlet 48 which extends generally perpendicular to the axis a of the inlet portion. At the bottom of inlet portion 40 there is a circumferential rim 50 having a tongue and groove arrangement which cooperates with the tongue and groove arrangement of a circumferential rim 52 carried by outlet portion 42.

Outlet portion 42 has a bottom wall 54 and upwardly extending sidewall portions 56 with a recessed area 58 having integrally formed adjacent thereto a male luer connector 60. Male luer connector 60 forms the outlet of the device and extends generally perpendicular to axis a, so that both the inlet 48 and outlet 60 are laterally disposed with respect to the connected inlet and outlet portions 40, 42, respectively.

Flexible palstic tubing 62 is connected to inlet 48 by pressure and adhesive bonding and a flexible plastic outlet tube 64 is pressure fitted over outlet 60. The inlet and outlet portions 40, 42 are isolated from each other by means of a fluid-impermeable membrane 66, which is preferably formed of EVA or PVC, with an illustrative example of suitable dimensions listed below.

Membrane 66 has a peripheral portion 68, an intermediate portion 70 and a central portion 72. Peripheral portion 68 is circular and includes an upwardly extending flange 74 which is received within a complimentary groove defined by inlet portion 40 (see FIG. 3) while the underside 76 of peripheral portion 68 rests on flange 52. Membrane 66 is formed in an integral, one-piece construction either by injection molding or thermoforming. Once formed, membrane 66 is sandwiched between inner and outer portions 40, 42.

Figure 5:
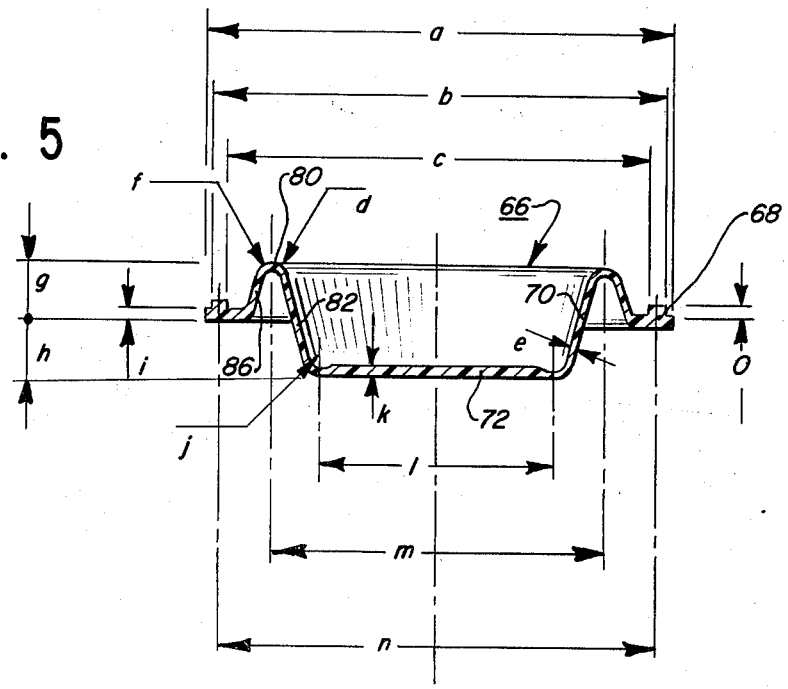
FIG. 5 is a cross-sectional view of a membrane used with the isolating apparatus of FIGS. 2–4.

Intermediate portion 70 extends from the outer peripheral portion 68 in a direction of top wall 44 and turns at 80 to have a curved portion 82 contiguous with the circumference 84 of central portion 72. As can be seen with reference to the cross-sectional illustration of the membrane 66 in FIGS. 3 and 5, intermediate portion 70 has a generally U-shaped cross-sectional configuration with one side 86 of the U being contiguous with outer peripheral portions 68, the other side 82 of the U being contiguous with central portion 72 and the bight 80 of the U being located in a plane between the outer peripheral portion 68 and top wall 44.

It is preferred that the central portion 72 be at least three times thicker than intermediate portion 82 in order to provide a superior displacement of the membrane. The following dimensions are illustrative only and no limitation is intended, but these dimensions have been found suitable for providing a satisfactory membrane 66:

| Reference Letter (FIG. 5) | Dimension (In mm.) |
| --- | --- |
| a | 78.5 |
| b | 75.5 |
| c | 71.5 |
| d | 2.3 radius |
| e | 0.3 |
| f | 2.0 radius |
| g | 8.5 |
| h | 8.5 |
| i | 1.5 |
| j | 3.0 radius |
| k | 1.0 |
| l | 40 |
| m | 56 |
| n | 73.5 |
| o | 2.0 |

A pressure isolator has been provided which is simple in construction and is easy to manufacture. The membrane can be injection molded, blow molded, pressure molded, or thermo-formed.

The pressure isolator of the present invention has a relatively flat design providing superior packaging capability. As a result of the construction of the membrane in association with the pressure chamber, there is a relatively large displacement volume, allowing a longer line between the unit and the pressure monitoring device.

Upwardly extending member 44 forms a sealing lid which permits a large joint area with less risks of leak. With solvent soluable materials, an additional safety can be obtained by solvent brushing the seal area on both sides.

In operation of the membrane, at the lowest pressure (for example 0 to 50 mm. mercury) central portion 72 deforms slightly. At higher pressures, the intermediate portion 70 rolls off while the central portion 72 remains unaffected. This permits achieving approximately 2 mm. of mercury deviation at 550 mm. of mercury for a total membrane displacement of about 17 mm.

Although an illustrative embodiment of the invention has been shown and described, it is to be understood that various modifications and substitutions may be made by those skilled in the art without departing from the novel spirit and scope of the present invention.

What is claimed is:

1. Apparatus for isolating a pressure-sensitive device from blood flowing in an extra-corporeal blood system and for transmitting the blood pressure from a blood flow line coupled to the pressure sensing device through the isolating apparatus, including a pressure chamber having an inlet coupled to the blood flow line and an outlet coupled to the pressure sensing device, and a membrane disposed transverse said chamber and surrounded by the chamber to segregate an inlet side of said chamber from an outlet side of said chamber, said membrane being fluid-impermeable and having its outer peripheral portion connected to the surrounding housing, comprising:

said membrane having a generally planar, circular central portion lying in a plane between the outer peripheral portion and the outlet side;

said membrane having an intermediate portion contiguous with and between the central portion and the outer peripheral portion, said intermediate portion extending from the outer peripheral portion in the direction of said inlet side and turning to have a curved portion contiguous with the circumference of said circular central portion, whereby said intermediate portion has a generally U-shaped cross-sectional configuration with one side of the U being contiguous with said outer peripheral portion, the other side of the U being contiguous with the central portion and the bight of the U being located in a plane between said outer peripheral portion and said inlet side;

said inlet coupled to the blood flow line being in communication with said inlet side; and said outlet coupled to the pressure sensing device being in communication with said outlet side.

2. Apparatus as described in claim 1, said central portion having a substantially greater thickness than the thickness of said intermediate portion.

3. Apparatus as described in claim 2, said central portion being at least three times thicker than said intermediate portion.

4. Apparatus as described in claim 1, said inlet including an inlet fitting which extends generally perpendicular to the axis of said pressure chamber.

5. Apparatus as described in claim 1, said outlet including an outlet fitting which extends generally perpendicular to the axis of said pressure chamber.

6. Apparatus as described in claim 5, said outlet fitting comprising a male luer connector.

7. Apparatus for isolating a pressure-sensitive device from blood flowing in an extra-corporeal blood system and for transmitting the blood pressure from a blood flow line coupled to the pressure sensing device through the isolating apparatus, including a pressure chamber having an inlet coupled to the blood flow line and an outlet coupled to the pressure sensing device, and a membrane disposed transverse said chamber and surrounded by the chamber to segregate an inlet side of said chamber from an outlet side of said chamber, said membrane being fluid-impermeable and having its outer peripheral portion connected to the surrounding housing, comprising:

said inlet coupled to the blood flow line being in communication with said inlet side and including an inlet fitting which extends generally perpendicular to the axis of said pressure chamber; and said outlet coupled to the pressure sensing device being in communication with said outlet side and including an outlet fitting which extends generally perpendicular to the axis of said pressure chamber;

said membrane having a generally planar, circular central portion lying in a plane between the outer peripheral portion and the outlet side;

said membrane having an intermediate portion contiguous with and between the central portion and the outer peripheral portion, said intermediate portion having a generally U-shaped cross-sectional configuration with one side of the U being contiguous with said outer peripheral portion, the other side of the U being contiguous with the central portion and the bight of the U being located in a plane between said outer peripheral portion and said inlet side; and said central portion having a substantially greater thickness than the thickness of said intermediate portion.

8. Apparatus as described in claim 7, said central portion being at least three times thicker than said intermediate portion.

9. Apparatus as described in claim 7, said outlet fitting comprising a male luer connector.

10. Apparatus as described in claim 7, said outer peripheral portion including an annular flange received within an annular groove defined by said pressure chamber.

11. Apparatus as described in claim 10, said annular flange being spaced inwardly from the outer periphery of said outer peripheral portion.

12. Apparatus as described in claim 7, said chamber comprising a pair of generally cylindrical mating portions, with one of said pair defining an annular groove, and said outer peripheral portion of said membrane including an annular flange received within said groove.

* * * * *